United States Patent [19]

Tai

[11] 4,404,115

[45] Sep. 13, 1983

[54] ENZYMATIC LIQUID CLEANING COMPOSITION

[75] Inventor: Ho T. Tai, Santes, France

[73] Assignee: Lever Brothers Company, New York, N.Y.

[21] Appl. No.: 439,961

[22] Filed: Nov. 8, 1982

[30] Foreign Application Priority Data

Nov. 13, 1981 [GB] United Kingdom ................. 8134310

[51] Int. Cl.[3] ........................ C11D 3/04; C11D 3/386; C11D 17/08; C12N 9/96

[52] U.S. Cl. .................................... 252/135; 252/173; 252/174.12; 252/DIG. 12; 252/DIG. 14; 435/188

[58] Field of Search ...................... 252/174.12, 97, 109, 252/DIG. 12, DIG. 14, 135, 173; 435/188

[56] References Cited

U.S. PATENT DOCUMENTS 3,714,050 1/1973 Gray .

4,034,038 7/1977 Vogel ................................ 260/462

4,243,543 1/1981 Guilbert et al. ............ 252/DIG. 12

FOREIGN PATENT DOCUMENTS 947213 5/1974 Canada .

47-35192 11/1972 Japan .

1590445 11/1976 United Kingdom .

2021142A 5/1979 United Kingdom .

2079305 1/1982 United Kingdom ........... 252/174.12

*Primary Examiner*—John E. Kittle

*Assistant Examiner*—Mukund J. Shah

*Attorney, Agent, or Firm*—Milton L. Honig; James J. Farrell

[57] ABSTRACT

Aqueous enzymatic liquid cleaning compositions, especially built liquid enzymatic detergent compositions, are disclosed which contain as enzyme stabilizer an alkalimetal pentaborate, optionally with an alkalimetal sulphite and/or a polyol. Preferred alkalimetal pentaborate is sodium pentaborate ($Na_2B_{10}O_{16}.10H_2O$).

7 Claims, No Drawings

ENZYMATIC LIQUID CLEANING COMPOSITION

This invention relates to aqueous liquid cleaning compositions, and in particular to liquid cleaning compositions containing enzymes.

Aqueous liquid enzymatic detergent compositions are well-known in the art. The major problem which is encountered with such compositions is that of ensuring a sufficient storage-stability of the enzymes in these compositions. There have already been various proposals for the inclusion of special stabilising agents in such enzymatic liquid cleaning compositions.

It has already been proposed, for example, to use boric acid or borates, with particular reference to sodium tetraborate, especially borax ($Na_2B_4O_7.1 OH_2O$) in aqueous liquid enzymatic cleaning compositions (see for example: Canadian Pat. No. 947 213; French Pat. No. 2 369 338; British Pat. No. 1 590 445 and Japanese Patent Application No. 47/35,192). British Patent Application GB No. 2 021 142A discloses another stabilising system for enzymes, comprising a water-dispersible anti-oxidant and a water-soluble polyol.

It has now been found that an enzymatic liquid cleaning composition can be stabilised more effectively by the inclusion therein of an alkali metal pentaborate which may be used preferably in conjunction with an alkali metal sulphite and/or a polyol.

In general the pentaborate is used in an amount of from 1–15% by weight, preferably from 3–10% by weight of the composition. A preferred alkali metal pentaborate for use in the present invention is sodium pentaborate, $Na_2B_{10}O_{16}.1OH_2O$.

The alkali metal sulphite can be present in an amount of up to 15% by weight, preferably up to 10% by weight of the composition. A preferred alkali metal sulphite is sodium sulphite.

The polyols which can be used in the present invention contain only C-, H- and O-atoms. They are free from other (functional) substituting atoms such as N-, S- and the like. The polyols should contain at least 2 hydroxy groups and may contain even up to 6 hydroxy groups. Typical examples of polyols particularly suitable for use in the present invention are diols such as 1.2 propane diol, ethylene glycol, erythritan, and polyols such as glycerol, sorbitol, mannitol, glucose, fructose, lactose, etc.

In general the polyol may be present in an amount of up to 15% by weight, preferably up to 10% by weight of the total composition.

Generally an effective stabilisation can be achieved with alkali metal pentaborate alone at a level of 6–15% by weight, preferably from 8–12% by weight, though levels of below 6% can also be effectively used in conjunction with an alkali metal sulphite and/or a polyol.

Advantageously the pH of the composition should preferably be kept at a level of about 7–8.2 to achieve the best possible results. However, on varying the pentaborate:sulphite ratio the composition may have a pH above 8.2 with equally good results.

Generally a total amount of pentaborate, sulphite and/or polyol used in the composition not exceeding 20% by weight of the composition will be sufficient to achieve effective stabilisation as long as the total amount of stabilising system comprising the pentaborate is not below the 6% by weight level.

The advantage of pentaborate is that, when used at the level as herein defined, it generally provides a buffering effect on its own at the optimal pH condition to the liquid composition, which on dilution in use gives a sufficiently alkaline pH for optimal detergency, which effect is not achievable with other boron compounds such as a tetraborate or metaborate.

The stabilising system of the invention can be used in aqueous enzymatic liquid compositions, but has particular applicability to built liquid enzymatic detergent compositions.

The enzymes to be incorporated can be proteolytic, amylolytic and cellulolytic enzymes as well as mixtures thereof. They may be of any suitable origin, such as vegetable, animal, bacterial, fungal and yeast origin. However, their choice is governed by several factors, such as pH activity and/or stability optima, thermostability, stability versus active detergents, builders and so on. In this respect bacterial or fungal enzymes are preferred, such as bacterial amylases and proteases, and fungal cellulases. Although the liquid compositions of the present invention may have a near-neutral pH value, the present invention is of particular benefit for enzymatic liquid detergents with a pH of between 7 and 8.2, especially those incorporating bacterial proteases of which the pH-optima lie in the range between 8.0 and 11.0, but it is to be understood that enzymes with a somewhat lower or higher pH-optimum can still be used in the compositions of the invention, benefiting from it.

Suitable examples of proteases are the subtilisins which are obtained from particular strains of B. subtilis and B. licheniformis, such as the commercially available subtilisins Maxatase® (ex Gist-Brocades N.V., Delft, Holland) and Alcalase® (ex Novo Industri A/S, Copenhagen, Denmark).

As stated above, the present invention is of particular benefit for enzymatic liquid detergents incorporating enzymes with pH-activity and/or stability optima of above 8.0, such as enzymes also commonly called high-alkaline enzymes.

Particularly suitable is a protease, obtained from a strain of Bacillus, having maximum activity throughout the pH-range of 8–12, developed and sold by Novo Industri A/S under the registered trade name of Esperase®. The preparation of this enzyme and analogous enzymes is described in British Patent Specification No. 1 242 784 of Novo.

High-alkaline amylases and cellulase can also be used, e.g. alpha-amylases obtained from a special strain of B. licheniformis, described in more detail in British Patent Specification No. 1 296 839 (Novo).

The enzymes can be incorporated in any suitable form, e.g. as a granulate (marumes, prills, etc.), or as a liquid concentrate. The granulate form often has advantages.

The amount of enzymes present in the liquid composition may vary from 0.001 to 10% by weight, and preferably from 0.01 to 5% by weight, depending on the enzyme activity. The activity of proteolytic enzymes is usually expressed in Anson units or glycine units (1 Anson unit/g=733 glycine units/mg).

When the liquid enzymatic compositions of the invention are detergent compositions, these liquid detergent compositions comprise as a further ingredient an active detergent material, which may be anionic, nonionic, cationic, zwitterionic, amphoteric detergent material, alkali metal or alkanol amine soaps of a $C_{10}$–$C_{24}$ fatty acid, or mixtures thereof.

Examples of anionic synthetic detergents are salts (including sodium, potassium, ammonium and substituted ammonium salts such as mono-, di- and triethanolamine salts) of $C_9$–$C_{20}$ alkylbenzene-sulphonates, $C_8$–$C_{22}$ primary or secondary alkane sulphonates, $C_8$–$C_{24}$ olefinsulphonates, sulphonated polycarboxylic acids, prepared by sulphonation of the pyrolyzed product of alkaline earth metal citrates, e.g. as described in British Patent Specification No. 1 082 179, $C_8$–$C_{22}$ alsulphates, $C_8$–$C_{24}$ alkylpolyglycol ether-sulphates (containing up to 10 moles of ethylene oxides); further examples are described in "Surface Active Agents and Detergents" (Vol. I and II) by Schwartz, Perry and Berch.

Examples of nonionic synthetic detergents are the condensation products of ethylene oxide, propylene oxide and/or butylene oxide with $C_8$–$C_{18}$ alkylphenols, $C_8$–$C_{18}$ primary or secondary aliphatic alcohols, $C_8$–$C_{18}$ fatty acid amides; further examples of nonionics include tertiary amine oxides with one $C_8$–$C_{18}$ alkyl chain and two $C_{1-3}$ alkyl chains. The above reference also describes further examples of nonionics.

The average number of moles of ethylene oxide and/or propylene oxide present in the above nonionics varies from 1–30; mixtures of various nonionics, including mixtures of nonionics with a lower and a higher degree of alkoxylation, may also be used.

Examples of cationic detergents are the quaternary ammonium compounds such, as alkyldimethyl ammonium halogenides, but such cationics are less preferred for inclusion in enzymatic detergent compositions.

Examples of amphoteric or zwitterionic detergents are N-alkylamino acids, sulphobetaines, condensation products of fatty acids with protein hydrolysates, but owing to their relatively high cost they are usually used in combination with an anionic or a nonionic detergent.

Mixtures of the various types of active detergents may also be used, and preference is given to mixtures of an anionic and a nonionic detergent active. Soaps in the form of their sodium, potassium, or substituted ammonium salts such as of polymerized fatty acids, may also be used, preferably in conjunction with an anionic and/or a nonionic synthetic detergent.

The amount of the active detergent material may vary from 1 to 60%, preferably from 2–40% and especially preferably from 5–25%; when mixtures of e.g. anionics and nonionics are used, the relative weight ratio varies from 10:1 to 1:10, preferably from 6:1 to 1:6. When a soap is also incorporated, the amount thereof is from 1–40% by weight.

A particularly preferred active detergent mixture is that of a water-soluble anionic sulphonate or sulphate detergent and a nonionic detergent in a weight ratio of from about 6:1 to 1:1, with or without a soap in a ratio of up to 2:1 with respect to the nonionic detergent constituent.

The liquid compositions of the invention may further contain up to 60%, preferably 5–50% by weight of a suitable builder, such as sodium, potassium and ammonium or substituted ammonium pyro- and tripolyphosphates, -ethylene-diamine tetraacetates, -nitrilotriacetates, -etherpolycarboxylates, -citrates, -carbonates, -orthophosphates, zeolites, carboxymethyloxysuccinate, etc. Particularly preferred are the polyphosphate builder salts, nitrilotriacetates, zeolites, and mixtures thereof.

The amount of water present in the detergent compositions of the invention can vary from 5 to 70% by weight.

Other conventional materials may also be present in the liquid detergent compositions of the invention, for example soil-suspending agents, hydrotropes, corrosion-inhibitors, dyes, perfumes, silicates, optical brighteners, suds boosters, suds depressants such as protected silicone compounds, germicides, anti-tarnishing agents, opacifiers, fabric softening agents, oxygen-liberating bleaches such as hydrogen peroxide, sodium perborate or percarbonate, diperisophthalic anhydride, with or without bleach precursors, buffers and the like.

Though on using the invention, the pH of the final composition can be kept at near neutral, preferably from 7–8.2, the pH of the wash liquor, on using the composition, will be in the alkaline range of well above 8 at an in-use concentration of about 1%.

The invention will now be illustrated by way of the following examples:

EXAMPLES I–II

Three enzymatic liquids of the following compositions were prepared and stored at 37° C.

| Composition (% by weight) | I | II | A |
|---|---|---|---|
| Na—dodecylbenzene sulphonate | 6.0 | 6.0 | 6.0 |
| Potassium soap | 2.4 | 2.4 | 2.4 |
| Nonionics | 3.5 | 3.5 | 3.5 |
| Sodium carboxy methylcellulose | 0.1 | 0.1 | 0.1 |
| Sodium toluene sulphonate | 1.0 | 1.0 | 1.0 |
| Sodium triphosphate | 25.0 | 25.0 | 25.0 |
| Fluorescent agent | 0.1 | 0.1 | 0.1 |
| Enzyme (Alcalase)* | 9GU/mg | 9GU/mg. | 9GU/mg |
| Sodium sulphite | — | 4.5 | 9.0 |
| Sodium pentaborate $10.H_2O$. | 9.0 | 4.5 | — |
| Perfume + water | | up to 100% | |
| pH of composition | 7.35 | 8.15 | 8.4 |
| pH (1% in distilled water) | 8.76 | 8.82 | 9.7 |
| pH (1% in very hard water) | 8.50 | 8.40 | 8.6 |
| % enzyme activity remaining after 2 weeks' storage at 37° C. | 50% | 50% | 0% |

*Alcalase of 1163 GU/mg (GU = glycine unit)

The enzyme stabilisation of the pentaborate formulation I and II according to the invention is evident.

EXAMPLE III

The same base liquid detergent composition of Examples I and II was used in the following experiments wherein the stabilising system was varied:

| System | (1) | (2) | (3) | (4) | (5) | (6) |
|---|---|---|---|---|---|---|
| Sodium tetraborate $5.H_2O$ | 4% | 9% | — | — | — | — |
| Sodium pentaborate $10.H_2O$ | — | — | 4% | 9% | — | — |
| Sodium metaborate $8.H_2O$ | — | — | — | — | 4% | 9% |
| (a) + 0% sulphite | | | | | | |
| pH (composition) | 8.61 | 8.51 | 7.76 | 7.19 | 10.27 | 11.36 |
| pH (1% solution) | 8.68 | 8.93 | 8.30 | 8.43 | 8.91 | 9.26 |
| (b) + 5% sulphite | | | | | | |
| pH (composition) | 8.58 | 8.49 | 7.66 | 7.01 | 9.80 | 11.34 |
| pH (1% solution) | 8.66 | 8.91 | 8.90 | 8.40 | 8.89 | 9.26 |
| (c) + 8% sulphite | | | | | | |
| pH (composition) | 8.60 | 8.52 | 7.65 | 7.16 | 10.26 | 11.48 |
| pH (1% solution) | 8.70 | 8.93 | 8.33 | 8.43 | 8.89 | 9.30 |

Comparison of enzyme activity after storage at 37° C.

| | |
|---|---|
| (1) (a) after two weeks | <10% |
| (2) (a) after two weeks | <10% |

-continued

| | |
|---|---|
| *(3) (a) after two weeks | 25% |
| *(4) (a) after two weeks | 40% |
| (5) (a) after two weeks | nil |
| (6) (a) after two weeks | nil |
| (1) (b) after two weeks | 50% |
| (2) (b) after two weeks | 55% |
| *(3) (b) after two weeks | 75% |
| *(4) (b) after two weeks | 100% |
| (5) (b) after two weeks | 10% |
| (6) (b) after two weeks | <10% |
| 1 (c) after three weeks | 70% |
| 2 (c) after three weeks | 60% |
| *3 (c) after three weeks | 70% |
| *4 (c) after three weeks | 100% |
| 5 (c) after three weeks | nil |
| 6 (c) after three weeks | nil |

*The above results show the overall superiority of the pentaborate stabilising system according to the invention over other borate systems outside the invention.

EXAMPLES IV-V

The following compositions were prepared:

| Compositions (% by weight) | IV | V |
|---|---|---|
| Alkylbenzene sulphonate | 6.0 | 6.0 |
| Triethanolamine soap | 2.4 | 2.4 |
| Nonionic | 3.5 | 3.5 |
| Sodium carboxy methylcellulose | 0.1 | 0.1 |
| Sodium toluene sulphonate | 1.0 | 1.0 |
| Sodium triphosphate | 25.0 | 25.0 |
| Fluorescent agent | 0.1 | 0.1 |
| Protease (Alcalase)* | 9GU/mg | 9GU/mg |
| Glycerol | 3.0 | — |
| Sodium sulphite | 4.5 | 5.0 |
| Sodium pentaborate $10.H_2O$ | 1.5 | 4.0 |
| Water + perfume | up to 100% | |
| pH (composition) | 7.92 | 7.70 |
| pH (1% in distilled water) | 8.40 | 9.00 |
| pH (1% in hard water) | 8.36 | 8.35 |
| Enzyme activity remaining after | | |
| 2 weeks' storage at 37° C. | 65% | 75% |
| 4 weeks' storage at 37° C. | 40% | 65% |

*Alcalase of 1163 GU/mg

From these results the beneficial effect of increased pentaborate level is clearly shown.

EXAMPLE VI

Similar compositions were prepared using the following enzyme-stabilizing system:

| | | |
|---|---|---|
| Glycerol | 5% | — |
| Sodium sulphite | — | 7% |
| Sodium pentaborate $10H_2O$ | 2% | 5% |
| pH (composition) | 7.7 | 7.6 |
| pH (1% in distilled water) | 9.1 | 9.0 |
| pH (1% in hard water) | 8.4 | 8.4 |
| Enzyme activity remaining after | | |
| 4 weeks' storage at 37° C. | 50% | — |
| 7 weeks' storage at 37° C. | — | 60% |

I claim:

1. Enzymatic liquid cleaning composition comprising:
   (a) from 0.001 to 10% by weight of an enzyme selected from the group consisting of proteolytic, amylolytic and cellulolytic enzymes and mixtures thereof;
   (b) from 1 to 15% by weight of an alkalimetal pentaborate;
   (c) from 0 to 15% by weight of an alkalimetal sulphite;
   (d) from 0 to 15% by weight of a polyol, containing from 2 to 6 hydroxy groups; and
   (e) water.

2. A composition according to claim 1, comprising from 3 to 10% by weight of said alkalimetal pentaborate.

3. A composition according to claim 1, which further comprises from 1 to 60% by weight of an active detergent material selected from the group consisting of anionic, nonionic, cationic, zwitterionic, amphoteric detergent materials, alkalimetal of alkanolamine soaps of $C_{10}$–$C_{24}$ fatty acids, and mixtures thereof; and from 0 to 60% by weight of a builder.

4. A composition according to claim 1, having a pH of from 7 to 8.2.

5. A composition according to claim 3, comprising:
   (a) from 0.01 to 5% by weight of enzyme;
   (b) from 1 to 15% by weight of alkalimetal pentaborate;
   (c) from 0 to 10% by weight of alkalimetal sulphite;
   (d) from 0 to 10% by weight of polyol;
   (e) from 2 to 40% by weight of active detergent material;
   (f) from 5 to 50% by weight of builder, selected from the group of polyphosphate builder salts, nitrilotriacetates, zeolites and mixtures thereof; and
   (g) from 5 to 70% by weight of water.

6. A composition according to claim 1, wherein said alkalimetal pentaborate is sodium pentaborate ($Na_2B_{10}O_{16}.10H_2O$), said alkalimetal sulphite is sodium sulphite, and said polyol is glycerol.

7. A composition according to claim 5, wherein the total amount of components (b), (c) and (d) is from 6 to 20% by weight of the composition.

* * * * *

UNITED STATES PATENT AND TRADEMARK OFFICE

CERTIFICATE OF CORRECTION

PATENT NO. : 4,404,115

DATED : September 13, 1983

INVENTOR(S) : Ho Tan Tai

It is certified that error appears in the above—identified patent and that said Letters Patent is hereby corrected as shown below:

Column 2, line 46, replace "1 242 784" with
-- 1 243 784 --.

Signed and Sealed this

*Eleventh* Day of *March 1986*

[SEAL]

*Attest:*

DONALD J. QUIGG

*Attesting Officer* *Commissioner of Patents and Trademarks*